United States Patent
Wen et al.

(10) Patent No.: US 10,702,869 B2
(45) Date of Patent: Jul. 7, 2020

(54) MINIATURIZED FLUID MANIPULATION SYSTEM

(71) Applicant: Taiwan Semiconductor Manufacturing Co., Ltd., Hsinchu (TW)

(72) Inventors: Chin-Hua Wen, Miaoli County (TW); Jui-Cheng Huang, Hsinchu (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 379 days.

(21) Appl. No.: 15/705,730

(22) Filed: Sep. 15, 2017

(65) Prior Publication Data
US 2019/0001333 A1 Jan. 3, 2019

Related U.S. Application Data

(60) Provisional application No. 62/526,111, filed on Jun. 28, 2017.

(51) Int. Cl.
*B01L 3/00* (2006.01)
*F16K 99/00* (2006.01)
(Continued)

(52) U.S. Cl.
CPC ... *B01L 3/502769* (2013.01); *B01L 3/502738* (2013.01); *F16K 99/0028* (2013.01); *G01N 15/0637* (2013.01); *G01N 15/0656* (2013.01); *G01N 27/3275* (2013.01); *G01N 27/4145* (2013.01); *G01N 33/5308* (2013.01); (Continued)

(58) Field of Classification Search
CPC ......... B01L 3/502769; B01L 3/502738; B01L 2400/0409; B01L 2400/0644; B01L 2400/0622; B01L 2300/0636; B01L 2300/0864; B01L 3/0224; B01L 3/022; B01L 3/502715; B01L 2200/027; B01L 2200/0663; B01L 2300/0627; B01L 2300/0867; G01N 27/4145; G01N 15/0656; G01N 15/0637; G01N 27/3275; G01N 33/5308; G01N 35/08; G01N 2015/0065; G01N 35/04; G01N 27/414; G01N 33/48721; G05D 16/2066; F16K 99/0028; F16K 27/003; F04B 53/10
See application file for complete search history.

(56) References Cited

U.S. PATENT DOCUMENTS

| | | | |
|---|---|---|---|
| 10,429,341 B2 * | 10/2019 | Liu | G01N 33/5438 |
| 2006/0078961 A1 * | 4/2006 | Chiu | B01L 3/0293 435/29 |
| 2016/0146203 A1 * | 5/2016 | Yuan | F16K 27/003 137/1 |

* cited by examiner

*Primary Examiner* — Lore R Jarrett
(74) *Attorney, Agent, or Firm* — Sterne, Kessler, Goldstein & Fox P.L.L.C.

(57) ABSTRACT

A fluidic testing platform and methods of its operation are described. The fluidic cartridge includes a first fluidic channel and a wheel assembly coupled to the first fluidic channel. The wheel assembly includes a center portion coupled to the first fluidic channel and designed to deliver fluid through one or more second fluidic channels that radiate outward from the center portion. The wheel assembly also includes a third fluidic channel arranged in a closed loop and one or more capillaries coupled to an outer surface of the third fluidic channel and arranged to radiate outward from the center portion. The wheel assembly is designed to rotate such that fluid is forced outward from the center portion through the one or more capillaries.

20 Claims, 13 Drawing Sheets

(51) Int. Cl.
*G01N 35/08* (2006.01)
*G01N 33/53* (2006.01)
*G05D 16/20* (2006.01)
*G01N 27/327* (2006.01)
*G01N 15/06* (2006.01)
*G01N 27/414* (2006.01)
*G01N 15/00* (2006.01)

(52) U.S. Cl.
CPC ......... *G01N 35/08* (2013.01); *G05D 16/2066* (2013.01); *B01L 2300/0636* (2013.01); *B01L 2300/0864* (2013.01); *B01L 2400/0409* (2013.01); *B01L 2400/0622* (2013.01); *B01L 2400/0644* (2013.01); *G01N 2015/0065* (2013.01)

800

FLOW FLUID INTO CENTER PORTION OF WHEEL ASSEMBLY — 802

ROTATE WHEEL ASSEMBLY — 804

FLOW FLUID INTO CAPILLARIES ON OUTER SURFACE OF WHEEL ASSEMBLY — 806

FORM DROPLET OF FLUID AT END OF A CAPILLARY — 808

LOWER WHEEL ASSEMBLY TOWARDS SENSOR SURFACE — 810

MINIATURIZED FLUID MANIPULATION SYSTEM

CROSS REFERENCE TO RELATED APPLICATIONS

This application claims the benefit of U.S. Provisional Application No. 62/526,111 filed Jun. 28, 2017, the disclose of which is incorporated by reference herein in its entirety.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

The interaction of the biological sample itself and the biosensor can be a challenge. Typically, a fluid containing the biological sample is pipetted directly over the sensing portion of the biosensor. This method leads to a large portion of the fluid sample not being used, and is time consuming to manually load each sensing area. Other fluid delivery systems involve the use of pumps that deliver fluid through tubing to the sensor area. Such systems are highly reliant on the precise operation of the pumps and any valves being used, and are difficult to maintain as they become smaller.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
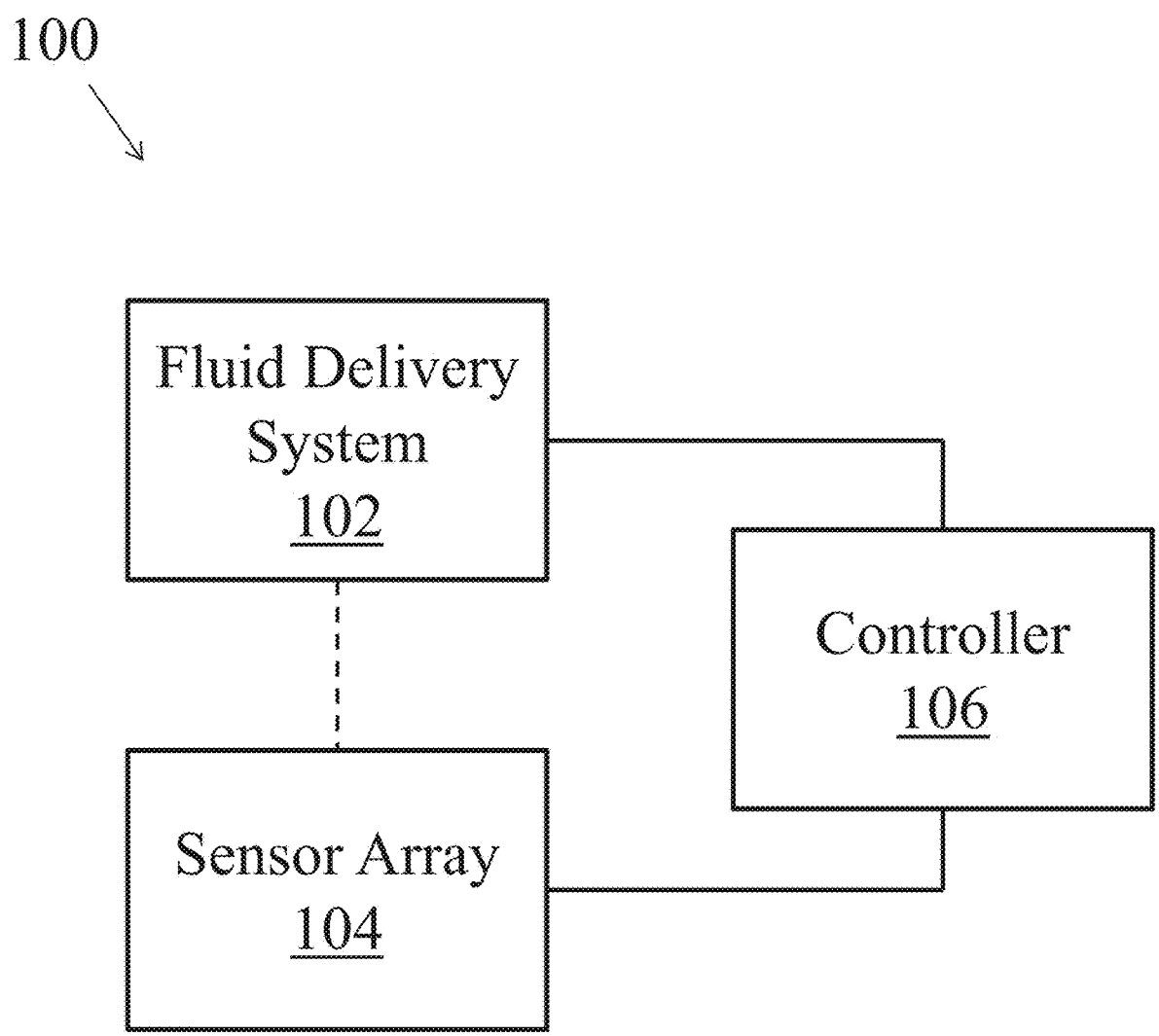
FIG. 1 is a diagram illustrating components of a fluidic testing arrangement.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, all technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies which are reported in the publications which might be used in connection with the invention.

The acronym "FET," as used herein, refers to a field effect transistor. A very common type of FET is referred to as a metal oxide semiconductor field effect transistor (MOSFET). Historically, MOSFETs have been planar structures built in and on the planar surface of a substrate such as a semiconductor wafer. But recent advances in semiconductor manufacturing have resulted in three-dimensional, fin-based MOSFET structures.

The term "bioFET" refers to a FET that includes a layer of immobilized capture reagents that act as surface receptors to detect the presence of a target analyte of biological origin. A bioFET is a field-effect sensor with a semiconductor transducer, according to an embodiment. One advantage of bioFETs is the prospect of label-free operation. Specifically, bioFETs enable the avoidance of costly and time-consuming labeling operations such as the labeling of an analyte with, for instance, fluorescent or radioactive probes. One specific type of bioFET described herein is a dual-gate back-side sensing bioFET. The analytes for detection by a BioFET will normally be of biological origin, such as—without limitation—proteins, carbohydrates, lipids, tissue fragments or portions thereof. However, in a more general sense a BioFET is part of a broader genus of FET sensors that may also detect any chemical compound (known in the art as a ChemFET), or any other element, including ions, such as protons or metallic ions (known in the art as an ISFET). This invention is meant to apply to all types of FET-based sensors ("FET Sensor"). One specific type of FET Sensor herein is a Dual-Gate Back Side Sensing FET Sensor ("DG BSS FET Sensor").

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "analysis" generally refers to a process or step involving, physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, ELISAs, and iqPCR), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and BCA assay), chemical assays (e.g., for the detection of environmental pollutants and contaminants, nanoparticles, or polymers and drug discovery assays. The apparatus, systems, and methods described herein may use or adopt one or more of these assays to be used with any of the FET Sensor described designs.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach using a body fluid sample has wide ranging implications in terms of patient welfare, the ability to conduct longitudinal disease monitoring, and the ability to obtain expression profiles even when tissue cells are not easily accessible, e.g., in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET Sensor may be used for detection of a target analyte (e.g., a tumor cell marker) in a liquid biopsy sample using a CTC assay. CTCs are cells that have shed into the vasculature from a tumor and circulate, e.g., in the bloodstream. Generally CTCs are present in circulation in extremely low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and IHC-based methods. For the apparatus, systems, and methods described herein, CTCs may be captured or detected using a capture reagent or the nucleic acids, proteins, or other cellular milieu from the CTCs may be targeted as target analytes for binding to or detection by a capture reagent.

When a target analyte is detected on or from a CTC, e.g., an increase in target analyte expressing or containing CTCs may help identify the subject as having a cancer that is likely to respond to a specific therapy (e.g., one associated with a target analyte) or allow for optimization of a therapeutic regimen with, e.g., an antibody to the target analyte. CTC measurement and quantitation can provide information on, e.g., the stage of tumor, response to therapy, disease progression, or a combination thereof. The information obtained from detecting the target analyte on the CTC can be used, e.g., as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes but is not limited to identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "reaction" refers to a physical, chemical, biochemical, or biological transformation that involves at least one chemical and that generally involves (in the case of chemical, biochemical, and biological transformations) the breaking or formation of one or more bonds such as covalent, noncovalent, van der Waals, hydrogen, or ionic bonds. The term includes typical chemical reactions such as synthesis reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, crystallization, dissolution, light emission, changes of light absorption or emissive properties, temperature change or heat absorption or emission, conformational change, and folding or unfolding of a macromolecule such as a protein.

"Capture reagent" as used herein, is a molecule or compound capable of binding the target analyte or target reagent, which can be directly or indirectly attached to a substantially solid material. The capture agent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte" as used herein, is the substance to be detected in the test sample using the present invention. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample" as used herein, means the composition, solution, substance, gas, or liquid containing the target analyte to be detected and assayed using the present invention. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to naturally-occurring and non-naturally occurring samples or combinations thereof. Naturally-occurring test samples can be synthetic or synthesized. Naturally-occurring test samples include body or bodily fluids isolated from anywhere in or on the body of a subject, including but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, e.g., nucleic acids (including DNA and RNA), hormones, different pathogens (including a biological agent that causes disease or illness to its host, such as a virus (e.g., H7N9 or HIV), a protozoan (e.g., Plasmodium-causing malaria), or a bacteria (e.g., *E. coli* or *Mycobacterium tuberculosis*), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include but are not limited to, e.g., pH changes, lactose changes, changing concentration, particles per unit time where a fluid flows over the device for a period of time to detect particles, particles that are sparse, and other parameters.

As used herein, the term "immobilized," when used with respect to, e.g., a capture reagent, includes substantially attaching the capture reagent at a molecular level to a surface. For example, a capture reagent may be immobilized to a surface of the substrate material using adsorption techniques including no covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based upon the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA comprising deoxyribonucleotides having any of adenine, guanine, cytosine, and thymine connected to each other and/or RNA comprising ribonucleotides having any of adenine, guanine, cytosine, and uracil connected to each other. In addition, non-naturally occurring nucleotides and non-naturally occurring nucleic acids are within the scope of the nucleic acid of the present invention. Examples include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substances for nucleic acid labeling known in the art can be used for labeling. Examples thereof include but are not limited to radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

Aptamer as used herein refers to oligonucleic acids or peptide molecules that bind to a specific target molecule. The concept of using single-stranded nucleic acids (aptamers) as affinity molecules for protein binding was initially disclosed in 1990 (Ellington and Szostak 1990, 1992 Tuerk and Gold 1990), and is based on the ability of short sequences to fold, in the presence of a target, into unique, three-dimensional structures that bind the target with high affinity and specificity. Eugene W. M. Ng et al., 2006, discloses that aptamers are oligonucleotide ligands that are selected for high-affinity binding to molecular targets.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component ($Cl_q$) of the classical complement system. (Kuby, Immunology, 4th ed., Chapter 4. W. H. Freeman & Co., New York, 2000).

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgD, IgA, and IgY), or subclass (e.g., IgG1, IgG2, IgG3, IgA1 and IgA2).

The term "polymer" means any substance or compound that is composed of two or more building blocks ('mers') that are repetitively linked to each other. For example, a "dimer" is a compound in which two building blocks have been joined together. Polymers include both condensation and addition polymers. Typical examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Exemplary Biosensing Testing Platform

FIG. 1 illustrates an overview of components that may be included in a biosensor testing platform 100. Biosensor testing platform 100 includes a fluid delivery system 102 designed to deliver one or more fluid samples to a sensor array 104. A controller 106 may be used to send and receive electrical signals to sensor array 104 to perform the bio or chemical sensing measurement. Controller 106 may also be used to send electrical signals to fluid delivery system 102 to, for example, actuate one or more valves, pumps, or motors. In another example, different controllers may be used to communicate with fluid delivery system 102 and sensor array 104.

Fluid delivery system 102 may include a variety of components designed to deliver controlled amounts of fluid to one or more sensors within sensor array 104. Each fluid may be delivered for a different purpose. For example, a first fluid may be delivered to functionalize a surface of one or more sensors in sensor array 104 with capture reagents. A different fluid may be delivered to provide target reagents to be captured by the capture reagents. Other fluids may be delivered to wash the sensor surface, or provide a controlled buffer solution for performing the sensor measurement.

Fluid delivery system 102 may include one or more chambers for holding the various fluids to be delivered to sensor array 104. Additionally, fluid delivery system 102 may include a network of fluidic channels for directing the various fluids to specific locations either within fluid delivery system 102 or towards sensor array 104. In order to control the flow of the fluids, fluid delivery system 102 may include one or more valves, pumps, and/or motors to provide a pressure differential or force on the fluid and cause it to flow. Some of the components of fluid delivery system 102 may be easily disposable and replaceable, allowing for the same fluid delivery system 102 to be used for multiple chemical or biological tests without contamination. Fluid delivery system 102 may be a handheld device having its own controller. An example fluid delivery system is described in further detail later with reference to FIGS. 6 and 7.

Sensor array 104 may include an array of bioFETs where one or more of the bioFETs in the array are functionalized to detect a particular target analyte. Different ones of the sensors may be functionalized using different capture reagents (for detecting different target analytes.) Further details regarding an example design of particular bioFETs and an example of the arrayed architecture is provided later.

Controller 106 may include one or more processing devices, such as a microprocessor, and may be programmable to control the operation of fluidic delivery system 102 and/or sensor array 104. In some embodiments, fluidic delivery system 102 and sensor array 104 each have their own programmable controller. The details of controller 106 itself are not important for the understanding of the embodiments described herein. However, the various electrical signals that may be sent and received from sensor array 104 will be discussed in more detail later.

Details regarding the design and operation of the sensor array 104 is provided first, followed by a detailed description of an example fluid delivery system that utilizes a wheel assembly to deliver a precise amount of fluid to a small area.

Dual Gate Back-Side FET Sensors

One example type of bioFET sensor is the dual gate back-side FET sensor. Dual gate back-side FET Sensors utilize semiconductor manufacturing techniques and biological capture reagents to form sensitive and easily arrayed sensors. While conventional MOSFETs have a single gate electrode that is connected to a single electrical node, the dual gate back-side sensing FET Sensor has two gate electrodes each of which is connected to a different electrical node. A first one of the two gate electrodes is referred to herein as the front-side gate and the second one of the two gate electrodes is referred to herein as the back-side gate. Both the front-side gate and the back-side gate are configured such that, in operation, each one may be electrically charged and/or discharged and thereby each influences the electric field between the source/drain terminals of the dual gate back-side sensing FET Sensor. The front-side gate is electrically conductive, separated from a channel region by a front-side gate dielectric, and configured to be charged and discharged by an electrical circuit to which it is coupled. The back-side gate is typically separated from the channel region by a back-side gate dielectric, and includes a biofunctionalized sensing layer disposed on the back-side gate dielectric. The amount of electric charge on the back-side gate is a function of whether a biorecognition reaction has occurred. In the typical operation of dual gate back-side sensing FET Sensors, the front-side gate is charged to a voltage within a predetermined range of voltages. The voltage on the front-side gate determines a corresponding conductivity of the FET Sensor's channel region. A relatively small amount of change to the electric charge on the back-side gate changes the conductivity of the channel region. It is this change in conductivity that indicates a biorecognition reaction.

One advantage of FET Sensors is the prospect of label-free operation. Specifically, FET Sensors enable the avoidance of costly and time-consuming labeling operations such as the labeling of an analyte with, for instance, fluorescent or radioactive probes.

Figure 2:
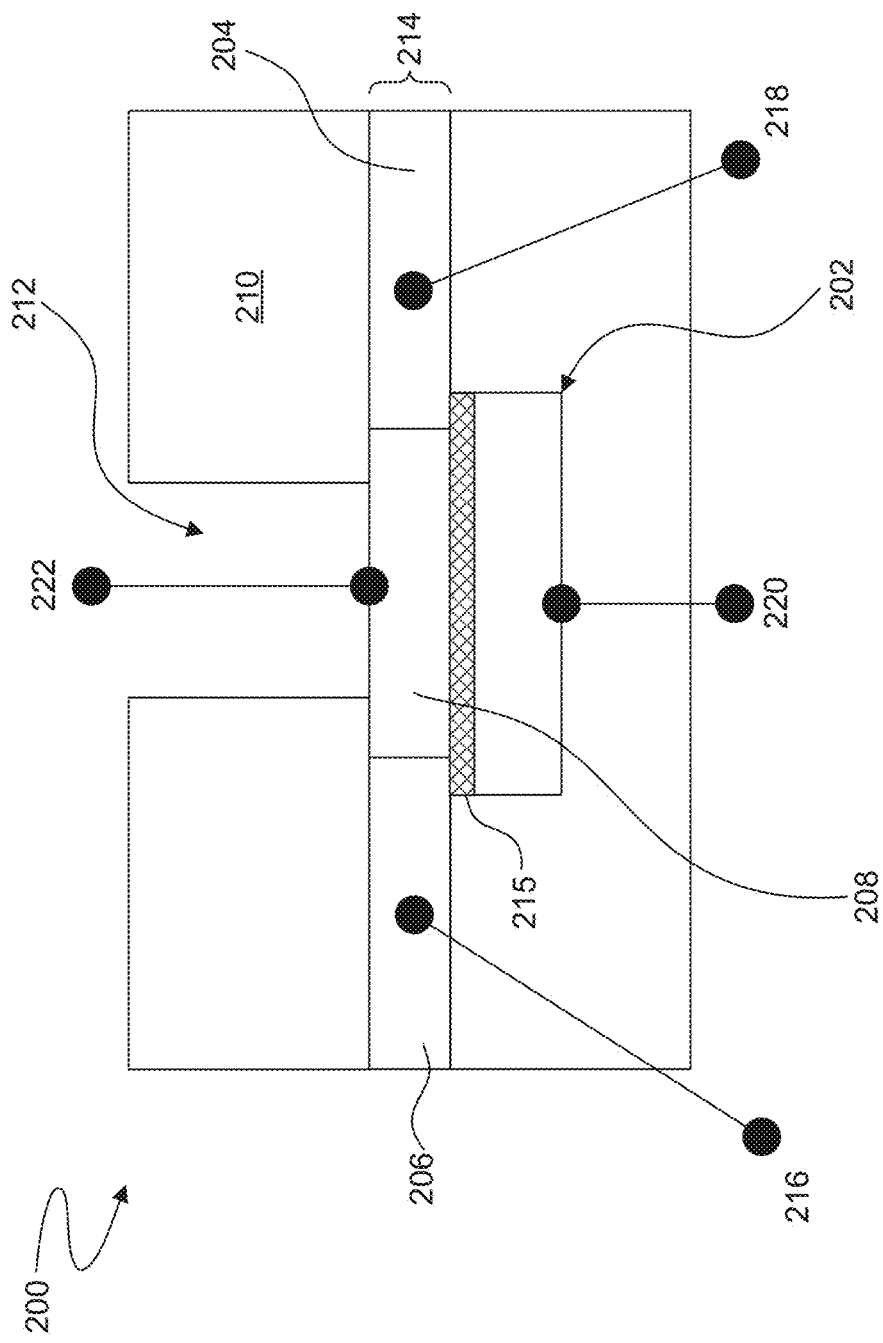
FIG. 2 is a cross-sectional view of an exemplary dual-gate back-side sensing FET Sensor.

Referring to FIG. 2, illustrated is an exemplary dual gate back-side sensing FET sensor 200. Dual gate back-side sensing FET sensor 200 includes a control gate 202 formed over substrate 214 and separated therefrom by an intervening dielectric 215 disposed on substrate 214. Substrate 214 further includes a source region 204, a drain region 206, and a channel region 208 between source region 204 and drain region 206. In an embodiment, substrate 214 has a thickness between about 100 nm and about 130 nm. Gate 202, source region 204, drain region 206, and channel region 208 may be formed using suitable CMOS process technology. Gate 202, source region 204, drain region 206, and channel region 208 form a FET. An isolation layer 210 is disposed on the opposing side of substrate 214 from gate 202. In one embodiment, isolation layer 210 has a thickness of about 1 μm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In other embodiments, opening 212 is larger than gate 202 and may extend over multiple dual gate back-side sensing FET Sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided herein.

Dual gate back-side sensing FET sensor 200 includes electrical contacts to drain region 206 (Vd 216), source region 204 (Vs 218), gate structure 202 (front-side gate 220), and/or active region 208 (e.g., back-side gate 222). It should be noted that back-side gate 222 does not need to physically contact substrate 214 or any interface layer over substrate 214. Thus, while a conventional FET uses a gate contact to control conductance of the semiconductor between the source and drain (e.g., the channel), dual gate back-side sensing FET sensor 200 allows receptors formed on the opposing side of the FET device to control the conductance, while gate structure 202 provides another gate to control the conductance. Therefore, dual gate back-side sensing FET sensor 200 may be used to detect one or more specific biomolecules or bio-entities in the environment around and/or in opening 212, as discussed in more detail using various examples herein.

Dual gate back-side sensing FET sensor 200 may be connected to additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), high voltage transistors, and/or high frequency transistors; other suitable components; and/or combinations thereof. It is further understood that additional features can be added in dual gate back-side sensing FET sensor 200, and some of the features described can be replaced or eliminated, for additional embodiments of dual gate back-side sensing FET sensor 200. Further details regarding example fabrication procedures of dual gate back-side sensing FET sensor 200 may be found in co-owned U.S. Patent Publication No. 2013/0200438 and U.S. Patent Publication No. 2014/0252421, the disclosures of which are incorporated by reference in their entireties.

Figure 3:
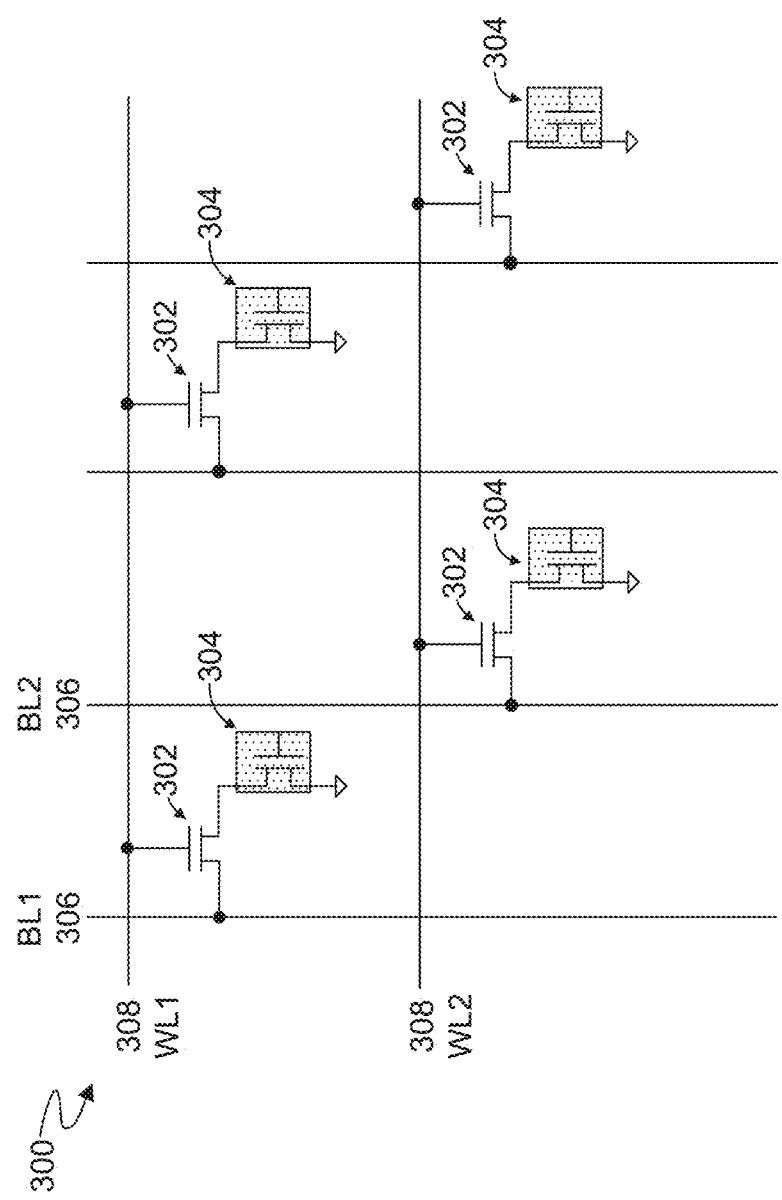
FIG. 3 is a circuit diagram of a plurality of FET Sensors configured in an exemplary addressable array.

Referring to FIG. 3, illustrated is a schematic of an exemplary addressable array 300 of FET Sensors 304 connected to bit lines 306 and word lines 308. It is noted that the terms bit lines and word lines are used herein to indicate similarities to array construction in memory devices, however, there is no implication that memory devices or a storage array necessarily be included in the array. Addressable array 300 may have similarities to that employed in other semiconductor devices such as dynamic random access memory (DRAM) arrays. For example, dual gate back-side sensing FET Sensor 200, described above with reference to FIG. 2, may be formed in a position that a capacitor would be found in a DRAM array. Schematic 300 is exemplary only and one would recognize other configurations are possible.

FET Sensors 304 may each be substantially similar to dual gate back-side sensing FET Sensor 200, FETs 302 are configured to provide connection between a drain terminal of FET Sensor 304 and bit line 306. In this way FETs 302 are analogous to access transistors in a DRAM array. In this exemplary embodiment, FET Sensors 304 is a dual gate back-side sensing FET Sensor and includes a sensing gate provided by a receptor material disposed on a dielectric layer overlying a FET active region disposed at a reaction site, and a control gate provided by a gate electrode (e.g., polysilicon) disposed on a dielectric layer overlying the FET active region.

Schematic 300 shows an array formation that may be advantageous in detecting small signal changes provided by minimal biomolecules or bio-entities introduced to FET Sensors 304. The arrayed format using bit lines 306 and word lines 308 allows for a decreased number of input/output pads. Amplifiers may be used to enhance the signal strength to improve the detection ability of the device having the circuit arrangement of schematic 300. In an embodiment, when particular word lines 308 and bit lines 306 are asserted, the corresponding access transistors 302 will be turned on (e.g., like a switch.) When the gate of the associated FET Sensor 304 (e.g., such as back-side gate 222 of the dual gate back-side sensing FET sensor 200) has its charge affected by the bio-molecule presence, FET Sensor 304 will transfer electrons and induce the field effect charging of the device, thereby modulating the current (e.g., $I_{ds}$). The change of the current (e.g., $I_{ds}$) or threshold voltage ($V_t$) can serve to indicate detection of the relevant biomolecules or bio-entities. Thus, the device having schematic 300 can achieve a biosensor application including application with differential sensing for enhanced sensitivity.

Figure 4:
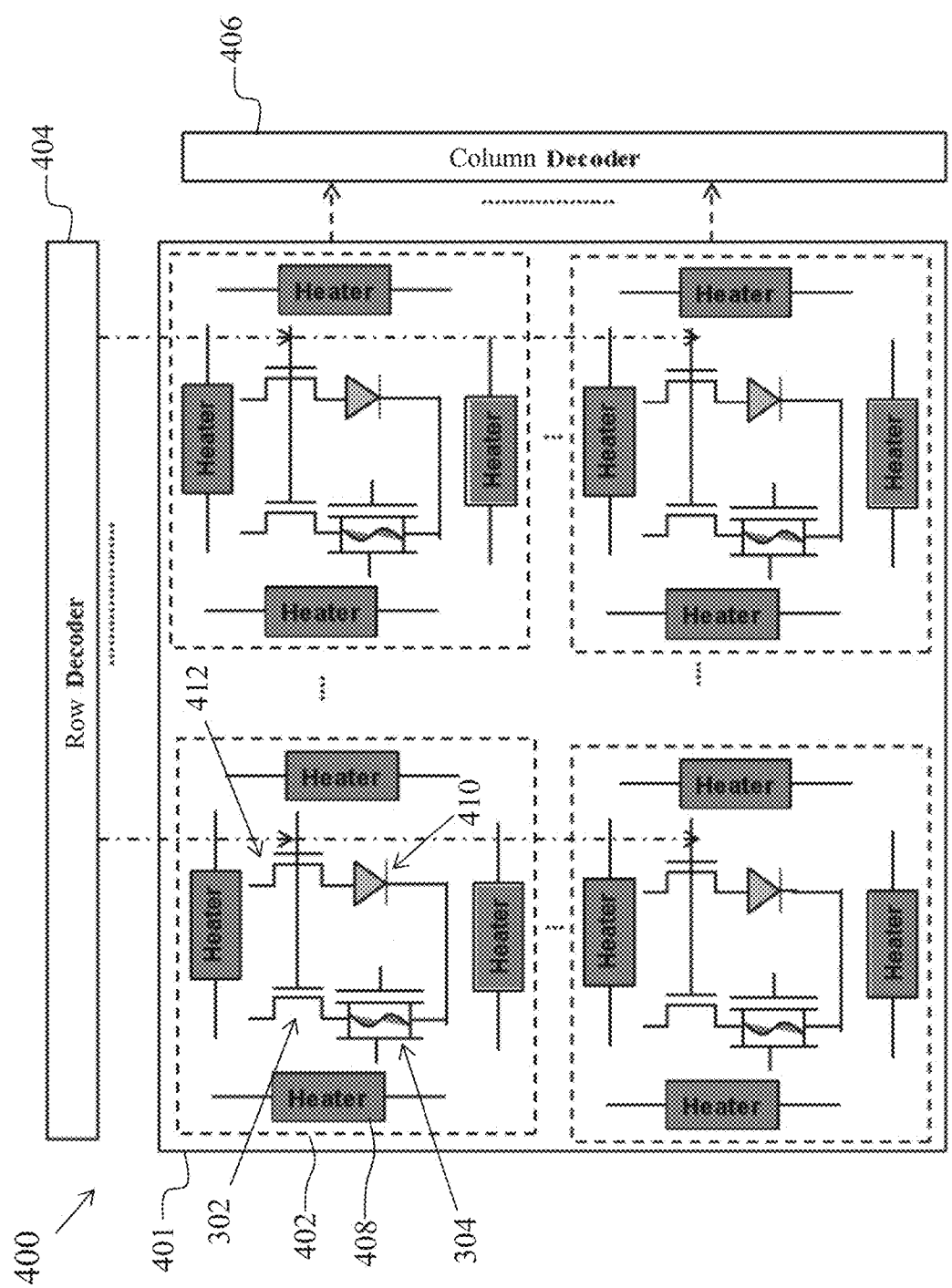
FIG. 4 is a circuit diagram of an exemplary addressable array of dual gate FET Sensors and heaters.

Referring to FIG. 4, an exemplary layout 400 is presented. Exemplary layout 400 includes access transistor 302 and FET Sensor 304 arranged as an array 401 of individually addressable pixels 402. Array 401 may include any number of pixels 402. For example, array 401 may include 128×128 pixels. Other arrangements may include 256×256 pixels or non-square arrays such as 128×256 pixels.

Each pixel 402 includes access transistor 302 and dual gate back-side sensing FET Sensor 304 along with other components that may include one or more heaters 408 and a temperature sensor 410. In this example, access transistor 302 is an n-channel FET. An n-channel FET 412 may also act as an access transistor for temperature sensor 410. In this illustrative example, the gates of FETs 302 and 412 are coupled in common, though this is not required. Each pixel 402 (and its associated components) may be individually addressed using column decoder 404 and row decoder 406. In one example, each pixel 402 has a size of about 10 micrometers by about 10 micrometers. In another example, each pixel 402 has a size of about 5 micrometers by about 5 micrometers, or has a size of about 2 micrometers by about 2 micrometers.

Column decoder 406 and row decoder 404 may be used to determine the ON/OFF state of n-channel FETs 302 and 412. Turning on n-channel FET 302 provides a current to an S/D region of dual gate back-side sensing FET Sensor 304. When these devices are ON, a current $I_{ds}$ flows through FET Sensor 304 and may be measured.

Heater 408 may be used to locally increase a temperature around a dual gate back-side sensing FET Sensor 304. Heater 408 may be constructed using any known technique, such as forming a metal pattern with a high current running through it. Heater 408 may also be a thermoelectric heater/cooler, like a Peltier device. Heater 408 may be used during certain biological tests, such as to denature DNA or RNA, or to provide a more ideal binding environment for certain biomolecules. Temperature sensor 410 may be used to measure the local temperature around dual gate back-side sensing FET Sensor 304. In one embodiment, a control loop may be created to control the temperature using heater 408 and the feedback received from temperature sensor 410. In another embodiment, heater 408 may be a thermoelectric heater/cooler that allows for local active cooling of the components within pixel 402.

Figure 5A:
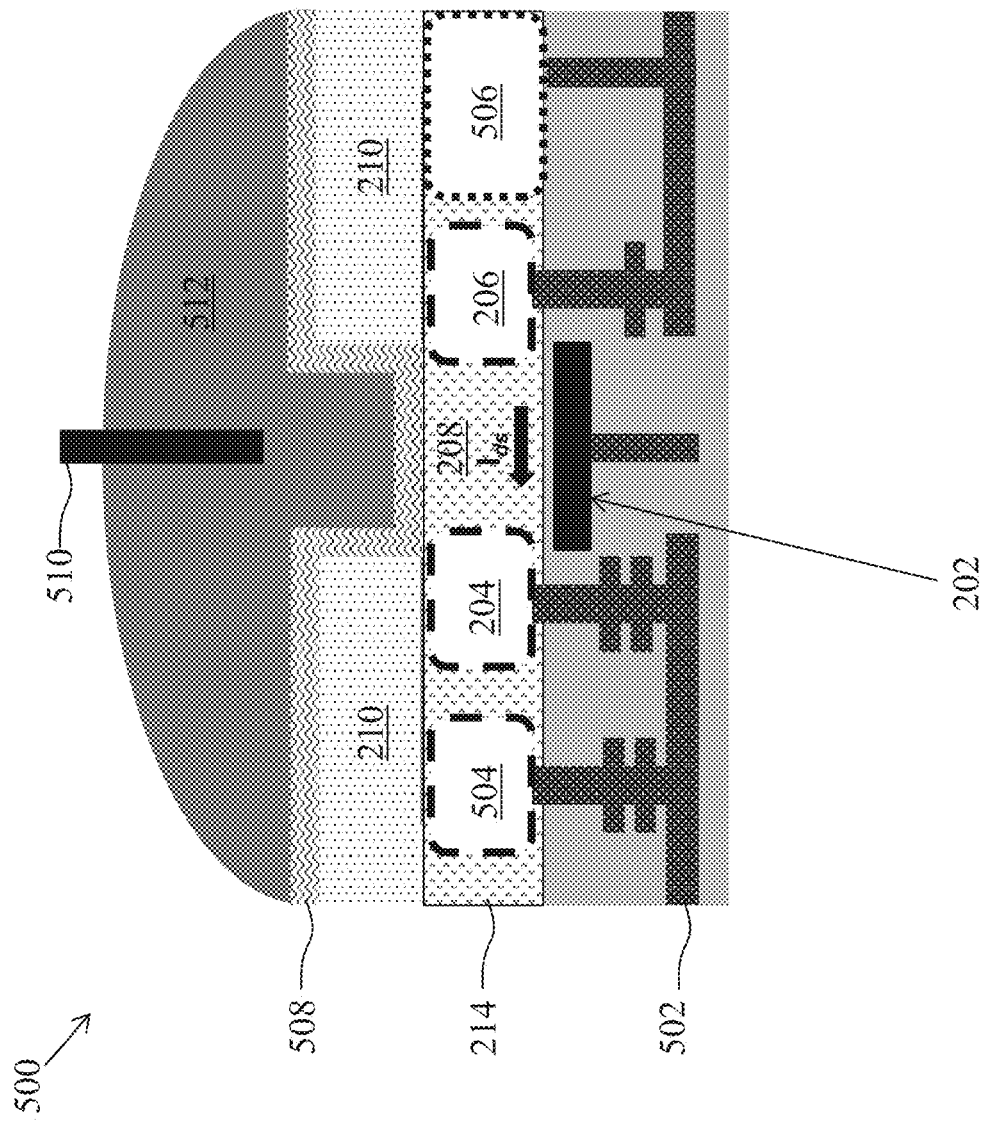
FIG. 5A is a cross-sectional view of an exemplary dual gate back-side sensing FET Sensor.

Referring to FIG. 5A, a cross section of an example dual gate back-side sensing FET Sensor 500 is provided. The dual gate back-side sensing FET Sensor 500 is one implementation of dual gate back-side sensing FET Sensor 200, thus previously described elements from FIG. 2 are labeled with element numbers from FIG. 2 and their descriptions are not repeated here. Dual gate back-side sensing FET Sensor 500 includes gate 202, source region 204, drain region 206, and channel region 208, where source region 204 and drain region 206 are formed within substrate 214. Gate 202, source region 204, drain region 206, and channel region 208 form a FET. It should be noted that the various components of FIG. 5A are not intended to be drawn to scale and are exaggerated for visual convenience, as would be understood by a person skilled in the relevant art.

In an exemplary embodiment, dual gate back-side sensing FET Sensor 500 is coupled to various layers of metal interconnects 502 that make electrical connection with the various doped regions and other devices formed within substrate 214. Metal interconnects 502 may be manufactured using fabrication processes well known to a person skilled in the relevant art.

Dual gate back-side FET Sensor 500 may include a body region 504 separate from source region 204 and drain region 206. Body region 504 may be used to bias the carrier concentration in active region 208 between source region 204 and drain region 206. As such, a negative voltage bias may be applied to body region 504 to improve the sensitivity of dual gate back-side FET Sensor 500. In one embodiment, body region 504 is electrically connected with source region 204. In another embodiment, body region 504 is electrically grounded.

Dual gate back-side FET Sensor 500 may be coupled to additional circuitry 506 fabricated within substrate 214. Circuitry 506 may include any number of MOSFET devices, resistors, capacitors, or inductors to form circuitry to aid in the operation of dual gate back-side sensing FET Sensor 500. For example, column decoder 406 and row decoder 404 may be formed in circuitry 506. Circuitry 506 may include any amplifiers, analog to digital converters (ADCs), digital to analog converters (DACs), voltage generators, logic circuitry and DRAM memory, to name a few examples. All or some of the components of additional circuitry 506 may be integrated in the same substrate 214 as dual gate back-side FET Sensor 500. It should be understood that many FET sensors, each substantially similar to dual gate back-side FET Sensor 500, may be integrated on substrate 214 and coupled to additional circuitry 506. In another example, all or some of the components of additional circuitry 506 are provided on another semiconductor substrate separate from substrate 214. In yet another example, some components of additional circuitry 506 are integrated in the same substrate 214 as dual gate back-side FET Sensor 500, and some components of additional circuitry 506 are provided on another semiconductor substrate separate from substrate 214.

Still referring to the illustrative example of FIG. 5A, dual gate back-side sensing FET Sensor 500 includes an interface layer 508 deposited over isolation layer 210 and within the opening over channel region 208. In one embodiment, interface layer 508 has a thickness between about 20 Å and about 40 Å. Interface layer 508 may be a high-K dielectric material, such as hafnium silicate, hafnium oxide, zirconium oxide, aluminum oxide, tantalum pentoxide, hafnium dioxide-alumina ($HfO_2$—$Al_2O_3$) alloy, or any combinations thereof. Interface layer 508 may act as a support for the attachment of capture reagents as will be discussed in more detail later in the section directed to biological sensing. A solution 512 is provided over the reaction site of dual gate back-side sensing FET Sensor 500, and fluid gate 510 is placed within solution 512. Solution 512 may be a buffer solution containing capture reagents, target reagents, wash solution, or any other biological or chemical species.

An example operation of dual gate back-side FET Sensor 500 acting as a pH sensor will now be described. Briefly, a fluid gate 510 is used to provide the electrical contact to the "second gate" of the dual gate back-side sensing FET Sensor. Solution 512 is provided over the reaction site of dual gate back-side sensing FET Sensor 500, and fluid gate 510 is placed within solution 512. The pH of the solution is generally related to the concentration of hydrogen ions [$H^+$] in the solution. The accumulation of the ions near the surface of interface layer 508 above channel region 208 will affect the formation of the inversion layer within channel region 208 that forms the conductive pathway between source region 204 and drain region 206. This can be measured by the change in the conductivity of the FET Sensor. In one embodiment, fluid gate 510 is used as the gate of the transistor during sensing while gate 202 remains floating. In another embodiment, fluid gate 510 is used as the gate of the transistor during sensing while gate 202 is biased at a given potential. For example, gate 202 may be biased at a potential between −2V and 2V depending on the application, while fluid gate 510 is swept between a range of voltages. In another embodiment, fluid gate 510 is biased at a given potential (or grounded) while gate 202 is used as the gate of the transistor (e.g., its voltage is swept across a range of potentials) during sensing. Fluid gate 510 may be formed from platinum or may be formed from any other commonly used material(s) for reference electrodes in electrochemical analysis. The most common reference electrode is the Ag/AgCl electrode, having a stable potential value of about 0.230 V.

Figure 5C:
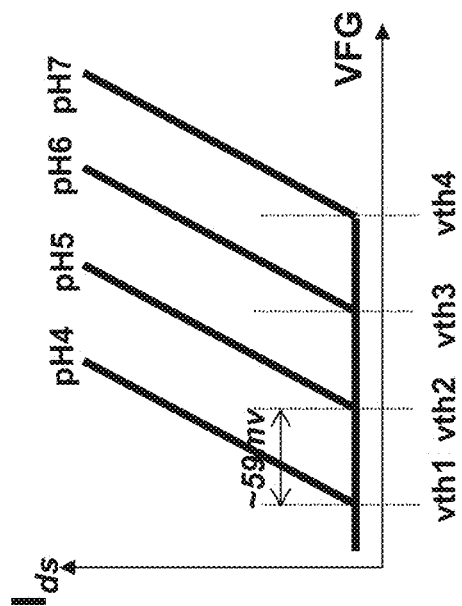
FIGS. 5B and 5C illustrate using the dual gate back-side sensing FET Sensor as a pH sensor.
Figure 5B:
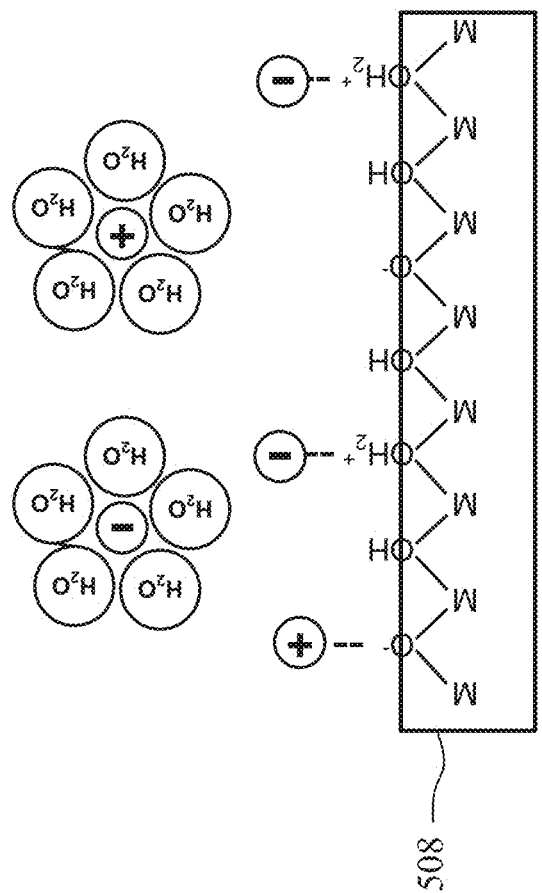

FIG. 5B shows ions in solution binding to a surface of interface layer 508. A top-most atomic layer of interface layer 508 is depicted as the various dangling [$O^-$], [OH], and

[OH$_2^+$] bonds. As the ions accumulate on the surface, the total surface charge affects the threshold voltage of the transistor. As used herein, the threshold voltage is the minimum potential between the gate and the source of a FET Sensor that is required to form a conductive path of minority carriers between the source and the drain of the FET sensor. The total charge also directly relates to pH of the solution, as a higher accumulation of positive charge signifies a low pH while a higher accumulation of negative charge signifies a high pH. FIG. 5C illustrates the change in threshold voltage that results due to different pH values in an n-channel Sensor. As can be observed in the figure, a 59 mV increase in threshold voltage roughly signifies an increase of one in the pH of the solution. In other words, one pH change results in total surface charge equivalent of 59 mV when measured as the voltage required to turn on the transistor.

Fluidic Testing Platform

Referring to the example FET sensor illustration in FIG. 5A, solution 512 is delivered over the sensor surface to perform the measurement. Precise delivery of solution 512 may be important to avoid wasting too much solution that is not being used for the sensing measurement. Furthermore, it may be desired to deliver solution 512 to only some of the sensors within the sensor array.

Figure 6:
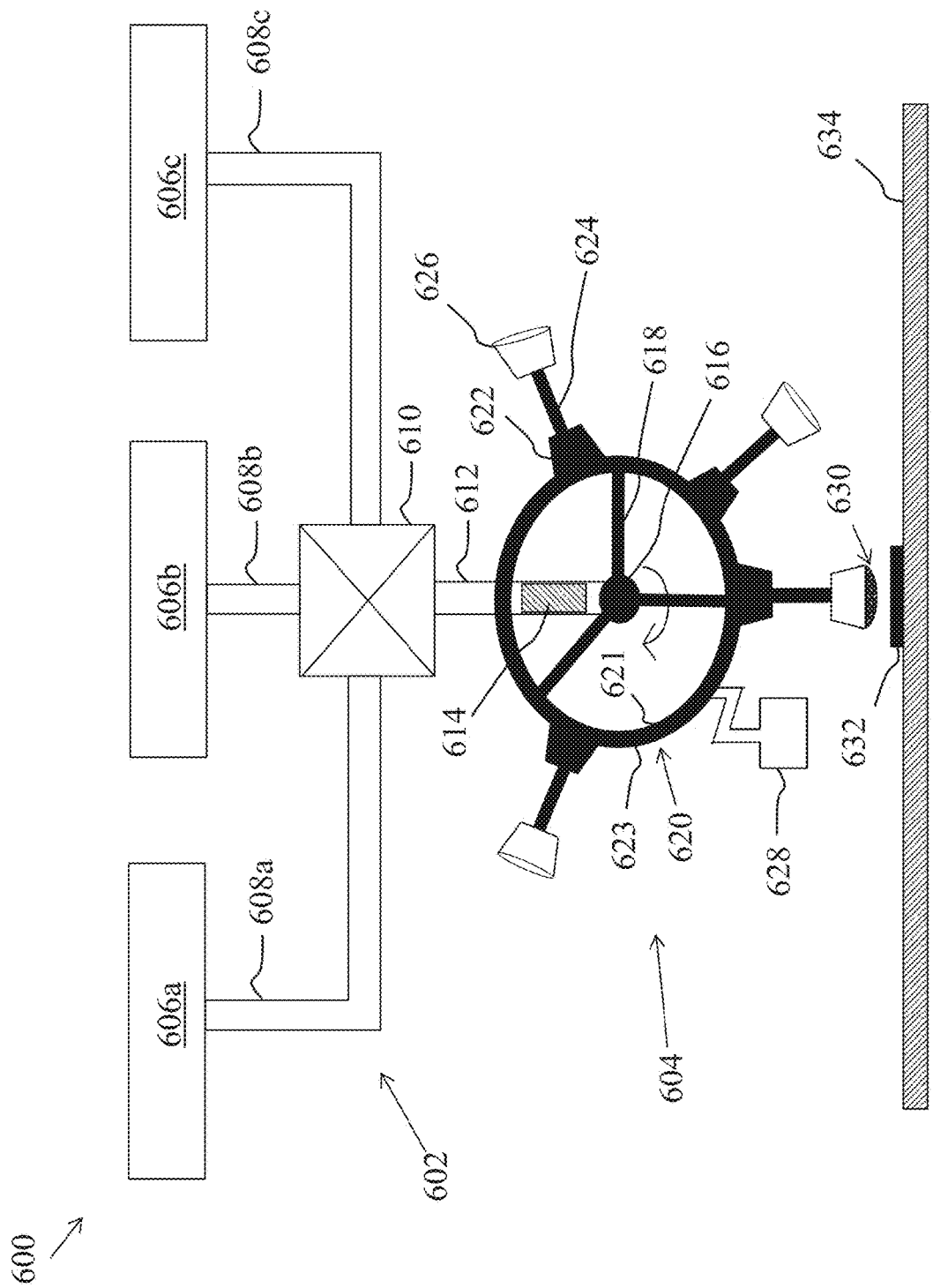
FIG. 6 illustrates a fluidic wheel assembly for delivering fluid to a sensor, according to an embodiment.

FIG. 6 illustrates an example of a fluidic testing platform 600, according to an embodiment. Fluidic testing platform may include two main sections: the first is a fluid handling assembly 602, and the second is a wheel assembly 604. Together, these sections operate together to deliver a precise droplet 630 of a given fluid to the surface of a sensor array 632 on a substrate 634. According to an embodiment, wheel assembly 604 rotates at a speed between about 600 RPM and about 1800 RPM to draw fluid from a first channel 612 and force the fluid outwards towards the openings at the ends of one or more cavities 626 displaced around the outer edge of wheel assembly 604.

Fluid handling assembly 602 includes a plurality of fluid chambers 606a-606c to hold various fluids that may be used for a particular assay or other biological/chemical test, according to an embodiment. Although only three chambers are illustrated, it would be understood that any number of fluid chambers may be included. In one example, each chamber is coupled via a corresponding fluid channel 608a-608c to a multi-way valve 610. Multi-way valve 610 may be an electrically controlled valve to allow fluid flow between only one of channels 608a-608c and first channel 612. Thus, multi-way valve 610 is designed to select a fluid path between one of chambers 606a-606c and wheel assembly 604. This fluid configuration is just one example, other fluid configurations using more than one valve may be used as well.

Each of chambers 606a-606c may hold a different solution to be used for a given test. For example, a first chamber 606a may include a solution containing capture reagents to immobilize on the surface of sensor array 632. A second chamber 606b may include a solution containing a sample to be tested (which may contain the target reagents). A third chamber 606c may include a buffer solution to use as a wash solution and to have over the sensor surface when performing a measurement. Each chamber 606a-606e may hold between about 1 mL and about 10 mL of fluid. Larger chambers 606a-606e may hold between about 5 mL and about 25 mL, or between about 10 mL and about 50 mL.

First fluidic channel 612 is coupled to an output of multi-way valve 610 to receive fluid from any of chambers 606a-606c. According to an embodiment, first fluidic channel 612 includes a reference electrode 614 to be used during the sensing measurement. Reference electrode 614 may operate in the same way as fluid gate 510 from FIG. 5A. As such, reference electrode 614 may be a platinum electrode, or a Ag/AgCl electrode. In one embodiment, first fluidic channel has a cross sectional area between about 2 mm$^2$ and about 4 mm$^2$. First fluidic channel 612 may be machined from a material such as stainless steel, or formed in a polymer material such as polydimethylsiloxane (PDMS) or polyethylene glycol (PEG). An outlet of first fluidic channel 612 may be coupled with a center portion 616 of wheel assembly 604.

Rotation of wheel assembly 604 forces fluid outwards to the edges of the assembly due to centrifugal force. This allows for the movement of fluid without needing a separate pump. While wheel assembly 604 is rotating, fluid may be drawn from first channel 612 up through center portion 616, which may include a hollow central column that rotates along with the other components of wheel assembly 604. Fluid flows through the hollow portion of center portion 616 and into one or more second channels 618, according to an embodiment. Second channels 618 radiate outward from center portion 616 and couple to an inner surface 621 of a third channel 620, arranged in a loop with its center axis aligned with center portion 616. Any number of second channels 618 may be used to direct fluid from center portion 616 into third channel 620. Each of second channels 618 and third channel 620 may be formed from a solid material, such as stainless steel. Third channel 620 may be arranged in a loop having a total diameter of between about 3 cm and about 7 cm. An inner fluid diameter of third channel 620 may be between about 1 mm and about 3 mm.

As wheel assembly 604 rotates, fluid is continually forced outward through funneling regions 622, coupled to an outer surface 623 of third channel 620, and into corresponding capillaries 624, according to an embodiment. Any number of capillaries 624 may be included around the outer edge of wheel assembly 604. According to an embodiment, capillaries 624 radiate outward from outer surface 623 of third channel 620. Capillaries 624 may be glass or stainless steel capillaries having an inner diameter ranging between about 0.5 mm and 1 mm. According to an embodiment, each capillary 624 may have substantially the same inner diameter such that droplets form at the end of each capillary 624 at substantially the same time for a given rotation speed of wheel assembly 604.

According to an embodiment, at the distal end of a capillary 624 is a cavity 626. Cavity 626 may be shaped like a cup and included to better control the size of the resulting droplet formed when the fluid reaches the end of capillary 624. Each cavity 626 may be a different size to form various-sized droplets. Cavity 626 may have a fluid volume between about 2 µL and about 20 µL.

A fluid droplet 630 is formed at the end of a given cavity 626 after the fluid has been pushed through the corresponding capillary 624, according to an embodiment. Once fluid droplet 630 has formed, wheel assembly 604 may be rotated such that droplet 630 is facing downwards towards sensor array 632. Fluidic testing platform 600, or just wheel assembly 604, may then be lowered until droplet 630 makes contact with the surface of sensor array 632. Droplet 630 may have a fluid volume of less than 1 µL, less than 100 nL, or less than 10 nL. Once droplet 630 has been delivered to sensor array 632, fluidic testing platform 600, or just wheel assembly 604, may be raised away from substrate 634.

Cavity 626 may also serve to maintain the formed droplet 630 after rotation of wheel assembly 604 has been slowed or stopped. After the centrifugal force has been removed from the fluid due to slowing or stopping of wheel assembly 604, the fluid in capillaries 624 may be drawn back toward third channel 620 due to capillary forces. But the fluid within cavity 626 has a greater volume such that the capillary force is not strong enough to draw back the fluid within cavity 626. Accordingly, in one embodiment, the size of cavity 626 is designed to maintain the fluid droplet 630 at cavity 626 even after rotation of wheel assembly 604 has been slowed or stopped.

Multiple fluid droplets may be formed for placing over various sensors in the sensor array (or a different sensor within a different sensor array). By using many capillaries 624 radiating outward from wheel assembly 604, fluid droplets may be formed at the end of each capillary 624 in a corresponding cavity 626 substantially simultaneously via rotation of wheel assembly 604. Once all droplets have been formed, each droplet may be placed over a different sensor by rotating wheel assembly 604 such that the target droplet is facing downward to be lowered onto the surface of sensor array 632. After a given droplet has been lowered onto a sensing surface, wheel assembly 604 may be rotated until a different capillary 624 is facing downward to provide another droplet to either another sensing surface or to the same sensing surface. In another example, a new fluid may be drawn up into wheel assembly 604 for making a new fluid droplet with the new solution.

Wheel assembly 604 may include a waste reservoir 628 coupled to an outer surface 623 of third channel 620. Waste reservoir 628 may be included to retrieve any excess fluid not being used to form droplets.

According to an embodiment, all components of wheel assembly 604 rotate together. As such, each of center portion 616, second channels 618, third channel 620, funnel regions 622, capillaries 624, cavities 626, and waste reservoir 628 all rotate at the same angular rate. A motor (not shown) may be used to rotate wheel assembly 604. Any type of electric motor may be used without limitation.

Various different fluids may be provided through first channel 612 and the channels of wheel assembly 604. Non-specific binding of various analytes within the different fluids to the walls of the channels can cause unwanted contamination. According to an embodiment, the inner walls of at least first channel 612, second channels 618, third channel 620, funnel regions 622, capillaries 624, and cavities 626 are coated with a material to reduce non-specific binding. The material may be used to increase the hydrophobicity of the inner walls. For example, bovine serum albumin (BSA) may be used to coat the inner walls of the various channels and reduce non-specific binding.

Figure 7:
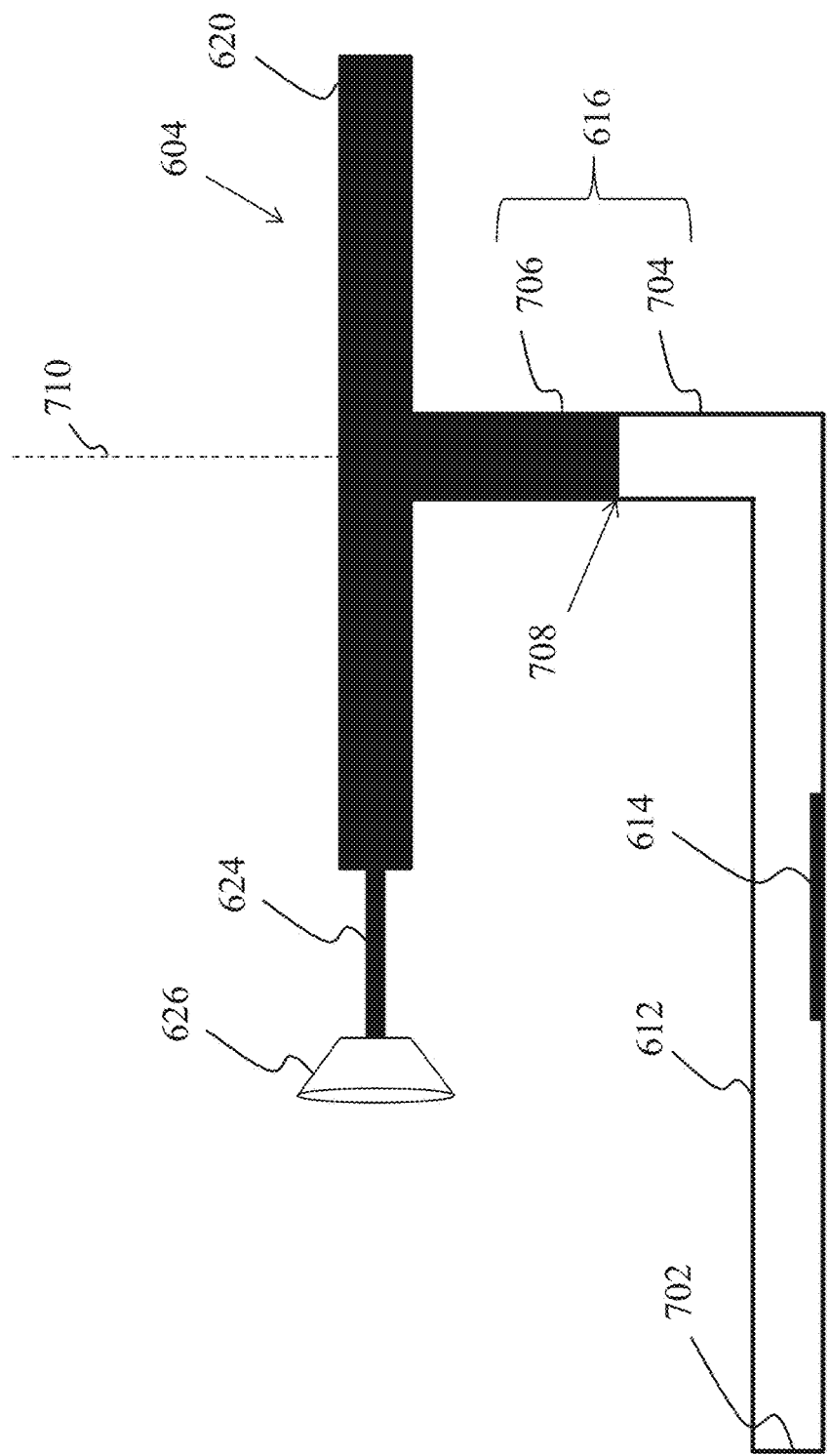
FIG. 7 illustrates a side view of the fluidic wheel assembly, according to an embodiment.

FIG. 7 illustrates a side view of fluidic testing platform 600 with a focus on the area where first channel 612 couples into center portion 616. Fluid flows from an inlet 702 of first channel 612, over reference electrode 614, and up into center portion 616. According to an embodiment, center portion 616 may include two sections, a lower section 704, which is static and coupled to first channel 612, and an upper section 706, which rotates along with the rest of wheel assembly 604. Both lower section 704 and upper section 706 have a hollow core for fluid to flow.

A sealing mechanism may be employed at an interface 708 between upper section 706 and lower section 704. The sealing may be performed using a polymer gasket or any other material commonly used to form a leak-proof seal. A bearing structure may also be provided at or near interface 708 to allow upper section 706 to rotate with reduced friction. In this side view, wheel assembly 604 would rotate about an axis 710 running vertically across the surface of the page, such that fluid would flow up through center portion 616 and outward through the second channels (not shown in this view) into third channel 620, capillary 624, and ultimately through cavity 626 to form a droplet to be delivered to a sensor surface.

According to an embodiment, wheel assembly 604 is disposable and replaceable. This can reduce contamination on future fluid deliveries using fluidic testing platform 600. In one example, wheel assembly 604 is removed at interface 708 and a new wheel assembly is coupled onto lower section 704 of center portion 616.

Figure 8:
FIG. 8 is a flow diagram of an exemplary method of using the fluidic wheel assembly, according to an embodiment.
Figure 8:
Figure 8:
Figure 8:
Figure 8:

Referring to FIG. 8, an example method 800 is presented. Method 800 may be performed by fluidic testing platform 600 to deliver a droplet of fluid to a surface of a sensor array. Other operations relating to fluid handling and electrical measurement not illustrated in method 800 may be performed either before, between, or after the illustrated operations of method 800. The various operations of method 800 may be performed in a different order than the one illustrated.

At block 802, fluid flows into a center portion of a wheel assembly. The fluid may first flow through a first channel that is coupled to the center portion. The fluid may be drawn into the center portion due to rotation of the wheel assembly. The fluid may be drawn from one or more chambers coupled to the first channel via one or more valves. The rate of fluid flow may be controlled based on the rotation speed of the wheel assembly.

At block 804, the wheel assembly is rotated. The operations of block 802 and 804 may occur substantially simultaneously, such that rotating the wheel assembly causes the fluid to flow. The wheel assembly may be rotated using an electric motor, such as an induction motor, or a stepper motor. According to an embodiment, the wheel assembly may be rotated at a speed between about 600 RPM and about 1800 RPM.

At block 806, fluid flows into capillaries disposed along an outer surface of the wheel assembly. The fluid may be continuously pushed outwards from the center of the wheel assembly through the capillaries due to centrifugal force while the wheel assembly is rotating.

At block 808, a droplet is formed at an end of a capillary. According to an embodiment, a cup-shaped cavity is disposed at the end of the capillary to control the shape and size of the droplet. Once the droplet has been formed, the wheel assembly may stop rotating to allow the droplet to be delivered to a sensor surface. The droplet may have a fluid volume of less than 1 μL, less than 100 nL, or less than 10 nL. In one embodiment, each of the capillaries has the same inner diameter and the same length such that multiple droplets formed at the ends of the capillaries are formed at substantially the same time.

At block 810, the wheel assembly is lowered towards the sensor surface such that the droplet makes contact with the sensor surface. The droplet may include capture reagents, target reagents, or may be used as a stable buffer solution over the sensor surface during a measurement. Rotation of the wheel assembly may be slowed or stopped in order to contact the droplet with the sensor surface.

Further operations may be performed using the fluidic testing platform in order to provide complete fluid delivery for each stage of an assay. In one example, block 810 may be repeated for each capillary having a droplet formed at its end. The wheel assembly may be rotated to position each capillary to be facing downward when delivering the droplet from the end of the given capillary. In another example, following block 810, the wheel assembly may be raised away from sensor surface and rotated to expel any excess fluid out of the wheel assembly or into a waste reservoir coupled to a portion of the wheel assembly. Once the first fluid has been adequately removed from the channels and capillaries of the wheel assembly, a second fluid may be drawn into the wheel assembly from another fluid chamber. The second fluid may be drawn into the wheel assembly by rotating the wheel assembly. Rotation of the wheel assembly may continue until a droplet of the second fluid is formed at the end of one or more of the capillaries. Once at least one droplet has been formed, the wheel assembly may again by lowered onto the sensor surface to deliver the droplet of the second fluid to the sensor.

The wheel assembly may be removed from a remaining portion of the fluidic testing platform in order to be disposed. A new wheel assembly may replace the disposed assembly on the fluidic testing platform, thus allowing for multiple tests to be performed without risk of contamination.

Chemistry, Biology and Interface

The apparatus, systems, and methods of the invention as described in this application can be used to deliver various fluids for the detection and/or monitoring of interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition the apparatus, systems, and methods of the invention can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, e.g., multiple target analytes.

Biological Sensing Examples with DGBSS FET Sensor

Figure 9:
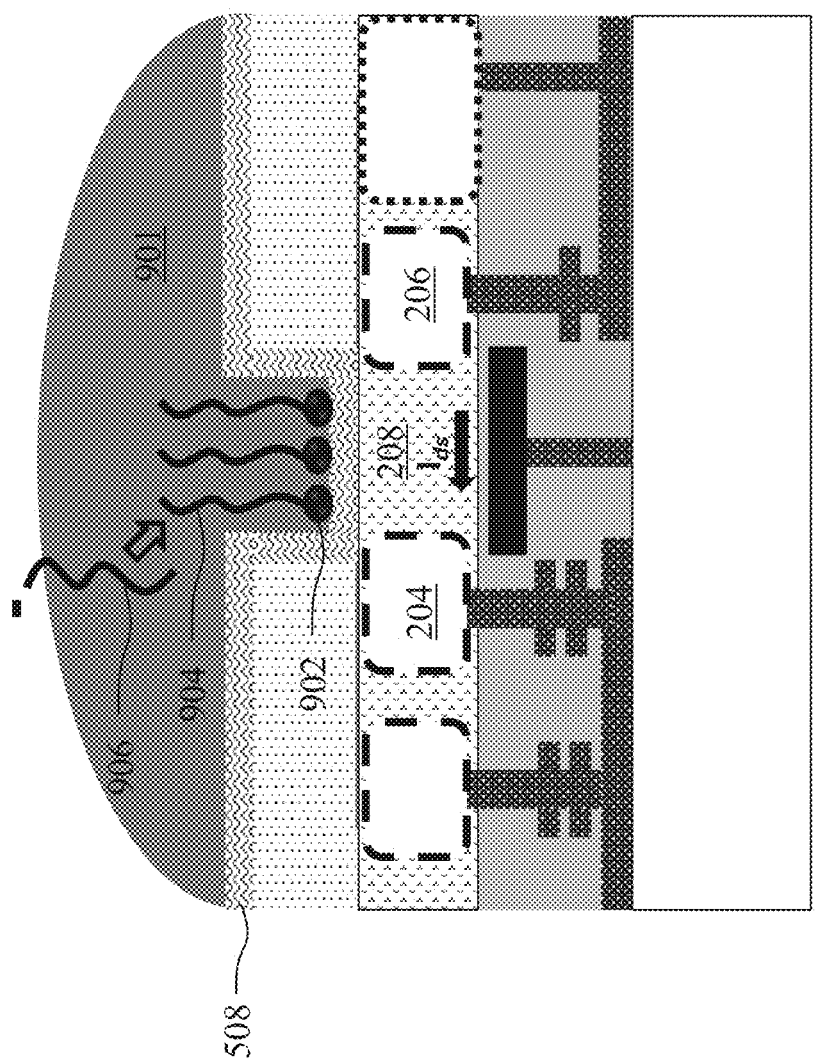
FIG. 9 is a cross-sectional view of an exemplary dual gate back-side sensing bioFET detecting DNA.

Referring to FIG. 9, an example biosensing test is performed using the dual gate back-side sensing FET Sensor described above in FIG. 5, Probe DNA 904 (an example of a capture reagent) is bound to interface layer 508 via a linking molecule 902. Linking molecule 902 may have a reactive chemical group that binds to a portion of interface layer 508. An example of linking molecules include thiols. Linking molecules may also be formed via silanization of the surface of interface layer 508, or by exposing the surface of interface layer 508 to ammonia ($NH_3$) plasma, in order to form reactive $NH_2$ groups on the surface. The silanization process involves sequentially exposing the surface of interface layer 508 to different chemicals to build up covalently-bound molecules on the surface of interface layer 508, as would be generally understood to a person skilled in the relevant art. Probe DNA 904 represent single stranded DNA. According to an embodiment, linking molecule 902 is bound to interface layer 508 before any steps of method 800 are performed. Probe DNA 904 may also be bound to linking molecule 902 before any steps of method 800 are performed. In another example, probe DNA 904 is bound to linking molecule 902 at block 810 of method 800. The dual gate back-side sensing FET sensor illustrated in FIG. 9 is one FET within a sensor array that would exist on a chip, according to an embodiment.

Probe DNA 904 may be immobilized on interface layer 508 prior to subjecting the FET Sensor to fluid sample 901. Fluid sample 901 may be delivered to the surface of the FET sensor using the fluidic testing platform 600. Fluid sample 901 may include the matching single stranded DNA sequence 906 that binds strongly to its matching probe DNA 904. The binding of additional DNA increases the negative charge present on interface layer 508, and directly above channel region 208 of the FET Sensor.

Figure 10B:
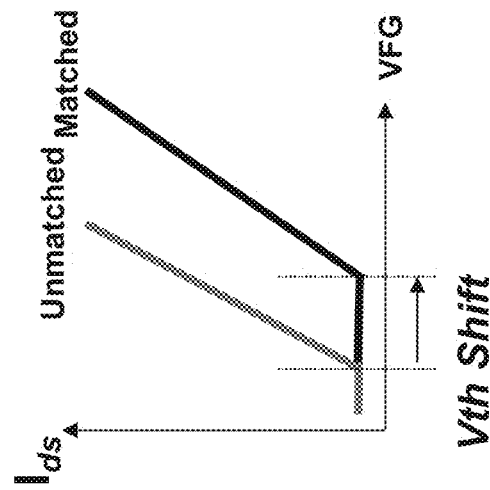
FIG. 10B illustrates a change in threshold voltage for the exemplary dual gate back-side sensing bioFET based on matched analyte binding.
Figure 10A:
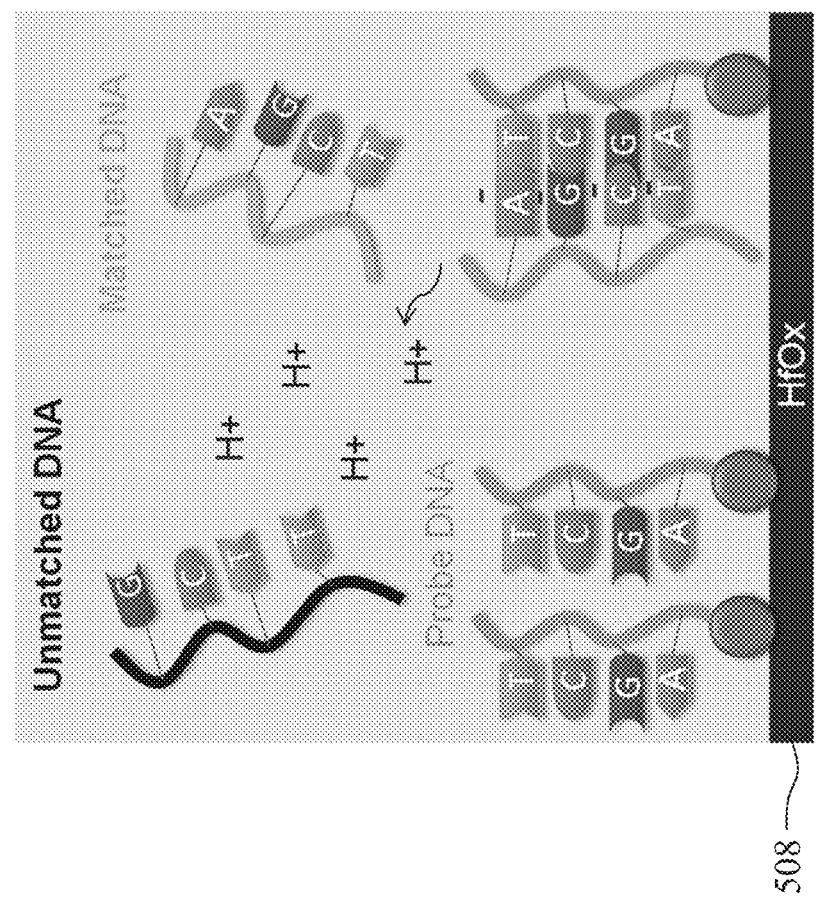
FIG. 10A illustrates the binding mechanics of DNA on a receptor surface.

The DNA binding is illustrated conceptually in FIG. 10A. Here probe DNA having nucleic acid sequence TCGA binds to its complementary matched strand having nucleic acid sequence AGCT. Any unmatched sequences will not hybridize with the probe DNA sequences. The binding of the matching DNA increases the negative charge built up at the interface of interface layer 508. In the example illustrated in FIG. 10A, interface layer 508 is hafnium oxide.

FIG. 10B illustrates a shift in the threshold voltage of the dual gate back-side sensing FET Sensor when matching DNA is bound to the surface of interface layer 508. Briefly, voltage is applied to the reference electrode until the FET Sensor "turns on" and current flows between drain region 206 and source region 204. The reference electrode is not illustrated in FIG. 9, but may be represented by reference electrode 614 as seen in FIGS. 6 and 7. When more negative charge is present at interface layer 508 due to complementary DNA binding, a higher voltage is required to form the conductive inversion layer within the channel region 208. Thus, according to an embodiment, a higher voltage may be applied to the reference electrode before the FET Sensor conducts and $I_{ds}$ current flows. This difference in threshold voltage may be measured and used to determine not only the presence of the target matching DNA sequence, but also its concentration. It should be understood that a net positive accumulated charge at interface layer 508 would cause the threshold voltage to decrease rather than increase. Additionally, the change in threshold voltage will have the opposite sign for an n-channel FET as compared to a p-channel FET.

Figure 11:
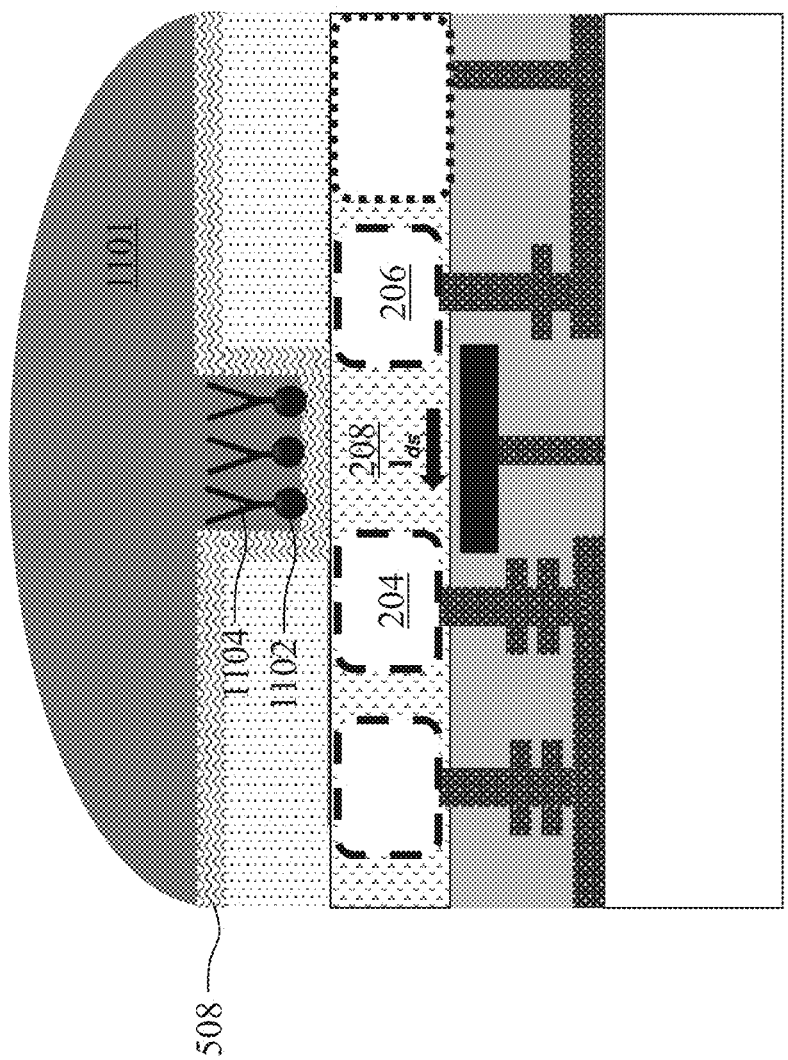
FIG. 11 is a cross-sectional view of an exemplary dual gate back-side sensing bioFET having antibodies immobilized on its sensing layer.

Referring to FIG. 11, another example biosensing test is performed using the dual gate back-side sensing FET Sensor. Probe antibodies 1104 (another example of capture reagents) are bound to interface layer 508 via linking molecules 1102. Linking molecules 1102 may have a reactive chemical group that binds to a portion of interface layer 508. A sample solution 1101 may be provided over probe antibodies 1104 to determine if the matching antigens are present within sample solution 1101. Sample solution 1101 may be delivered to the surface of the FET sensor using the fluidic testing platform 600. According to an embodiment, linking molecules 1102 are bound to interface layer 508 before any steps of method 800 are performed. Probe antibodies 1104 may also be bound to linking molecules 1102 before any steps of method 800 are performed. In another example, probe antibodies 1104 are bound to linking molecules 1102 at block 810 of method 800.

Figure 12:
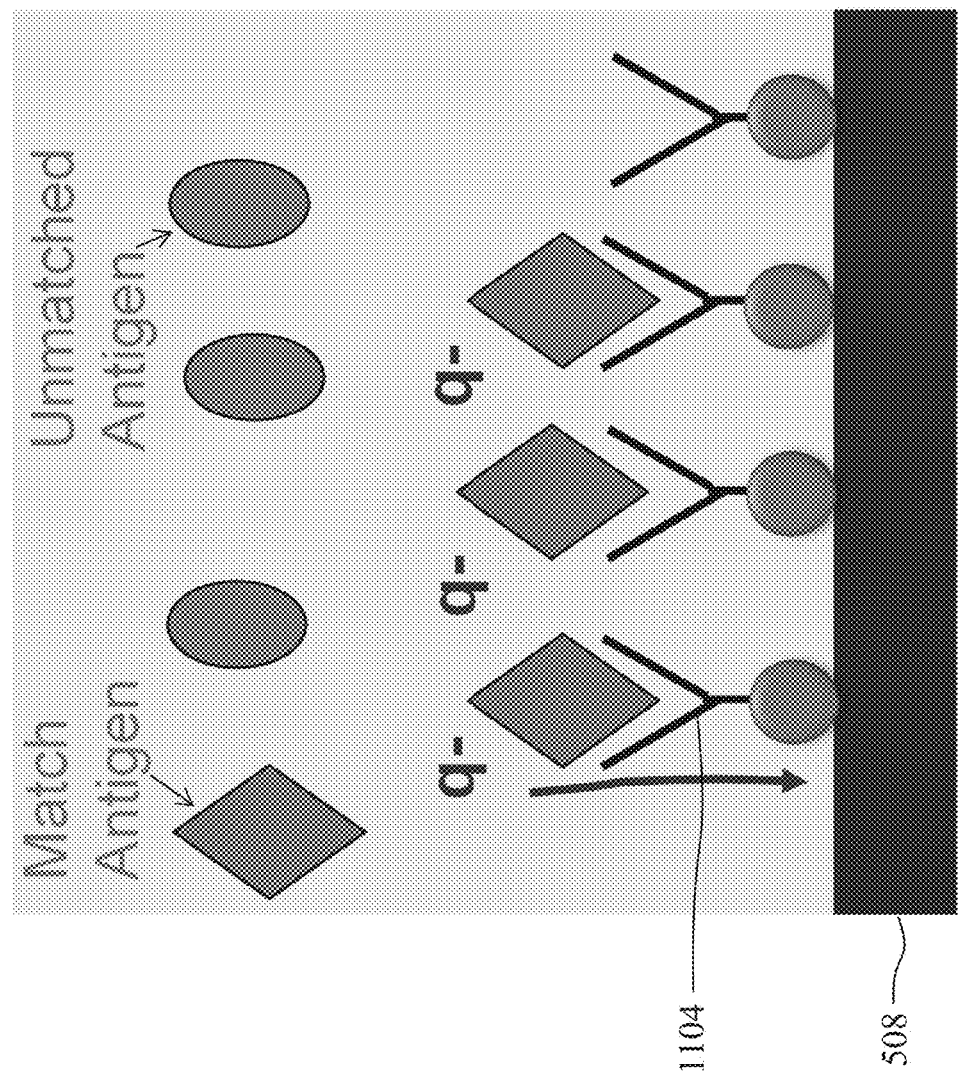
FIG. 12 illustrates the binding mechanics of antigens and antibodies on a receptor surface.

Referring to FIG. 12, the binding process of matching antigens to probe antibodies 1104 is illustrated. Here, matching antigens will bind to the immobilized probe antibodies while unmatched antigens will not bind. Similar to the DNA hybridization process described above, the matching antigens will change the accumulated charge present at interface layer 508. The shift in threshold voltage due to the accumulated charge from matching antibodies binding to the probe antibodies is measured in substantially the same way as already discussed above with reference to FIG. 10B.

Final Remarks

Described herein are embodiments of a fluid delivery device. According to an embodiment, the fluid delivery device includes a first fluidic channel having an inlet and an outlet, and a wheel assembly coupled to the outlet of the first fluidic channel. The wheel assembly includes a center portion coupled to the outlet of the first fluidic channel. The center portion is designed to deliver fluid through one or more second fluidic channels that radiate outward from the center portion. The wheel assembly also includes a third fluidic channel arranged in a closed loop, where each of the one or more second fluidic channels are coupled to an inner surface of the third fluidic channel. The wheel assembly also includes one or more capillaries coupled to an outer surface of the third fluidic channel and arranged to radiate outward from the center portion. The wheel assembly is designed to rotate such that fluid is forced outward from the center portion through the one or more capillaries.

According to another embodiment, a fluidic testing platform includes a first chamber designed to hold a first fluid, a second chamber designed to hold a second fluid, a multi-way valve designed to select between a fluid path from the first chamber and a fluid path from the second chamber, and a first fluidic channel coupled to an output of the multi-way valve. The fluidic testing platform also includes a wheel assembly coupled to the first fluidic channel. The wheel assembly includes a center portion coupled to an outlet of the first fluidic channel. The center portion is designed to deliver fluid through one or more second fluidic channels that radiate outward from the center portion. The wheel assembly also includes a third fluidic channel arranged in a closed loop, where each of the one or more second fluidic channels are coupled to an inner surface of the third fluidic channel. The wheel assembly also includes one or more capillaries coupled to an outer surface of the third fluidic channel and arranged to radiate outward from the center portion. The wheel assembly is designed to rotate such that fluid is forced outward from the center portion through the one or more capillaries.

An example method of delivering fluid to a sensor is described. The method includes flowing a fluid through a first channel and into a center portion of a wheel assembly and rotating the wheel assembly such that the fluid is forced outward from the center portion of the wheel assembly. The method also includes moving the fluid through one or more capillaries arranged on an outer surface of the wheel assembly, where the moving occurs due to the rotation of the wheel assembly. The method also includes forming a droplet of fluid at an end of one of the one or more capillaries, and lowering the wheel assembly towards a substrate having the sensor, such that the droplet makes contact with the sensor.

It is to be appreciated that the Detailed Description section, and not the Abstract of the Disclosure section, is intended to be used to interpret the claims. The Abstract of the Disclosure section may set forth one or more but not all exemplary embodiments of the present invention as contemplated by the inventor(s), and thus, is not intended to limit the present invention and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the subjoined claims and their equivalents.

What is claimed is:

1. A fluid delivery device, comprising:
a first fluidic channel having an inlet and an outlet; and
a wheel assembly coupled to the outlet of the first fluidic channel, the wheel assembly comprising:
a center portion coupled to the outlet of the first fluidic channel and configured to deliver fluid through one or more second fluidic channels that radiate outward from the center portion;
a third fluidic channel arranged in a closed loop, wherein each of the one or more second fluidic channels are coupled to an inner surface of the third fluidic channel;
a waste reservoir physically connected to an outer surface of the third fluidic channel, wherein the waste reservoir and the third fluidic channel are configured to rotate at a same angular speed; and
one or more capillaries coupled to the outer surface of the third fluidic channel and arranged to radiate outward from the outer surface of the third fluidic channel, wherein the wheel assembly is configured to rotate such that fluid is forced outward from the center portion through the one or more capillaries.

2. The fluid delivery device of claim 1, further comprising an electrode disposed within the first fluidic channel.

3. The fluid delivery device of claim 1, wherein each of the one or more capillaries comprises a cupped structure forming a cavity disposed at an end of the capillary.

4. The fluid delivery device of claim 3, wherein the cavity holds between 2 microliters and 20 microliters of fluid.

5. The fluid delivery device of claim 1, wherein the wheel assembly further comprises funnel regions coupled to the third fluidic channel and the one or more capillaries.

6. The fluid delivery device of claim 1, wherein the wheel assembly is designed to be removable from the first fluidic channel.

7. The fluid delivery device of claim 1, wherein a diameter of the wheel assembly as measured between the closed loop of the third fluidic channel is between 3 cm and 5 cm.

8. A fluidic testing platform, comprising:
a first chamber configured to hold a first fluid;
a second chamber configured to hold a second fluid;
a multi-way valve configured to select between a fluid path from the first chamber and a fluid path from the second chamber;
a first fluidic channel coupled to an output of the multi-way valve;
a wheel assembly coupled to the first fluidic channel, the wheel assembly comprising:
a center portion coupled to the first fluidic channel and configured to deliver fluid through one or more second fluidic channels that radiate outward from the center portion,
a third fluidic channel arranged in a closed loop, wherein each of the one or more second fluidic channels are coupled to an inner surface of the third fluidic channel, and
one or more capillaries coupled to an outer surface of the third fluidic channel and arranged to radiate outward from the outer surface of the third fluidic channel, wherein the wheel assembly is configured to rotate such that fluid is forced outward from the center portion through the one or more capillaries; and
a reference electrode disposed between an inlet of the first fluidic channel and a static portion of the center portion.

9. The fluidic testing platform of claim 8, wherein the multi-way valve is configured to choose between the fluid path from the first chamber and the fluid path from the second chamber based on received electric signals.

10. The fluidic testing platform of claim 8, wherein the reference electrode is disposed on an inner surface of the first fluidic channel.

11. The fluidic testing platform of claim 8, wherein each of the one or more capillaries comprises a cupped structure forming a cavity disposed at an end of the capillary.

12. The fluidic testing platform of claim 11, wherein the cavity holds between 2 microliters and 20 microliters of fluid.

13. The fluidic testing platform of claim 8, wherein the wheel assembly further comprises a waste reservoir coupled to the third fluidic channel.

14. The fluidic testing platform of claim 8, wherein the wheel assembly is designed to be removable from the first fluidic channel.

15. The fluidic testing platform of claim 8, wherein a diameter of the wheel assembly as measured between the closed loop of the third fluidic channel is between 3 cm and 5 cm.

16. A method of delivering fluid to a sensor, the method comprising:
- flowing a fluid through a first channel and into a center portion of a wheel assembly;
- rotating the wheel assembly at an angular speed such that the fluid is forced outward from the center portion of the wheel assembly;
- moving the fluid through one or more capillaries arranged on an outer surface of the wheel assembly, wherein the moving occurs due to the rotation of the wheel assembly;
- forming a droplet of fluid at an end of one of the one or more capillaries;
- lowering the wheel assembly towards a substrate having the sensor, such that the droplet makes contact with the sensor; and
- rotating a waste reservoir at the angular speed of the wheel assembly to retrieve a portion of the fluid.

17. The method of claim 16, wherein forming the droplet comprises forming a droplet having a size less than 10 nL.

18. The method of claim 16, further comprising stopping the rotation of the wheel assembly before lowering the wheel assembly towards the substrate having the sensor.

19. The method of claim 16, further comprising:
- raising the wheel assembly after the droplet makes contact with the sensor;
- rotating the wheel assembly until the fluid has been pushed out of the wheel assembly through the one or more capillaries;
- flowing a second fluid through the first channel and into a center portion of a wheel assembly;
- rotating the wheel assembly such that the second fluid is forced outward from the center portion of the wheel assembly;
- moving the second fluid through the one or more capillaries, wherein the moving occurs due to the rotation of the wheel assembly;
- forming a droplet of the second fluid at an end of one of the one or more capillaries;
- lowering the wheel assembly towards a substrate having the sensor, such that the droplet of the second fluid makes contact with the sensor.

20. The method of claim 16, further comprising removing the wheel assembly from the first channel and coupling another wheel assembly with the first channel.

* * * * *